United States Patent [19]

Bargery et al.

[11] Patent Number: 5,006,339
[45] Date of Patent: Apr. 9, 1991

[54] ANTI-VIRAL WIPE

[75] Inventors: Robert A. Bargery, Wirral; Gordon C. Peterson, Cheshire, both of Great Britain

[73] Assignee: Unilever Patent Holdings B.V., Rotterdam, Netherlands

[21] Appl. No.: 382,129

[22] Filed: Jul. 19, 1989

[30] Foreign Application Priority Data

Jul. 19, 1988 [GB] United Kingdom ............... 8817199

[51] Int. Cl.$^5$ .................. A61F 13/40; A61L 15/18; A61L 15/20
[52] U.S. Cl. .................. 424/404; 424/443; 424/405; 424/447; 604/306; 604/289; 604/358; 428/286; 428/284
[58] Field of Search ............ 424/400, 402, 404, 405, 424/443, 447; 604/1, 2, 306, 289, 358; 428/286, 284

[56] References Cited

U.S. PATENT DOCUMENTS

| | | | |
|---|---|---|---|
| 2,066,946 | 1/1937 | Reiman | 424/443 |
| 3,386,619 | 6/1968 | Douglas | 604/306 |
| 3,580,254 | 5/1971 | Stuart | 604/306 |
| 3,636,922 | 1/1972 | Ketner | 604/289 |
| 4,252,119 | 2/1981 | Coates | 604/306 |
| 4,522,953 | 6/1985 | Barby et al. | 521/150 |
| 4,575,891 | 3/1986 | Valente | 604/289 |
| 4,605,401 | 8/1986 | Chmelir et al. | 428/286 |
| 4,643,725 | 2/1987 | Schlesser et al. | 604/306 |

FOREIGN PATENT DOCUMENTS

| | | | |
|---|---|---|---|
| 0211664 | 7/1986 | European Pat. Off. | |
| 0230133 | 7/1987 | European Pat. Off. | |
| 5998 | of 1884 | United Kingdom | 424/443 |
| 0646075 | 11/1950 | United Kingdom | |
| 1443086 | 7/1976 | United Kingdom | 424/443 |
| 2083748 | 3/1982 | United Kingdom | 424/443 |

Primary Examiner—Thurman K. Page
Assistant Examiner—James M. Spear
Attorney, Agent, or Firm—Cushman, Darby & Cushman

[57] ABSTRACT

Packaged sheet-like article for wiping surfaces, said article comprising a highly absorbent material, capable of absorbing and retaining a hydrophilic liquid, and of reversibly releasing at least some of the liquid on application of hand pressure, and further containing an anti-viral agent. The highly absorbent material is contained between two sheets of material, at least one of them being permeable to the liquid.

9 Claims, 1 Drawing Sheet

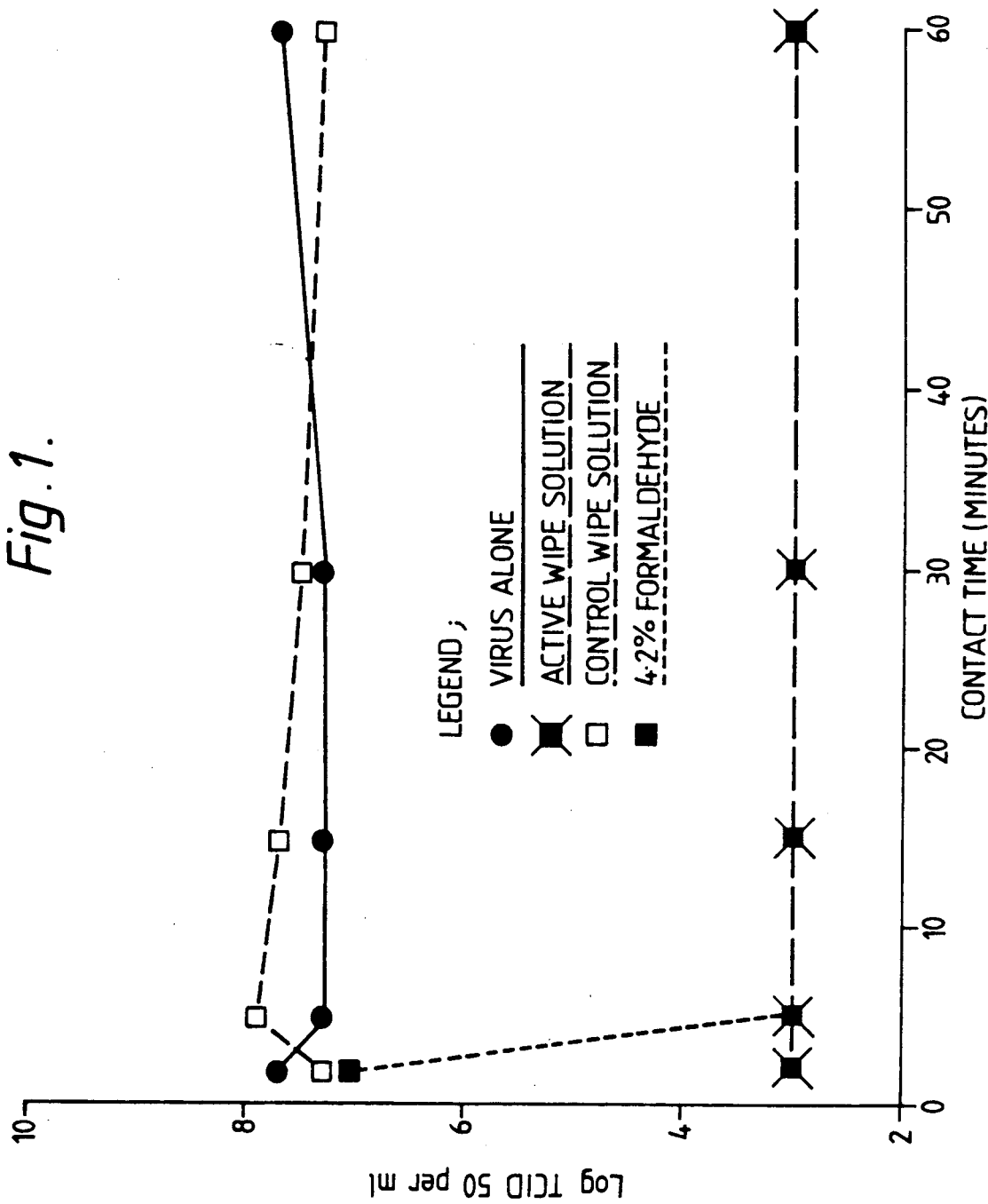

ANTI-VIRAL WIPE

The invention relates to a package containing a sheet-like article for wiping and disinfecting surfaces. More in particular, it relates to a package containing an anti-viral wipe.

There is an increasing public concern about the possibility of becoming infected with serious diseases such as Hepatitis B and Acquired Immune-Deficiency Syndrome (AIDS) by contact with spillages of body fluids, particularly blood, from individuals who are carrying the disease. Especially in certain professions, such as the medical profession, the chances of accidentally getting into contact with infected blood are far from negligible. It has therefore been suggested in the European patent application 230,133 that blood spillages be disinfected by scattering thereon a powdered or granular effervescent composition containing a source of available chlorine.

There are, however, certain drawbacks to this method. For instance, when blood is contacted with the effervescent composition, it starts to solidify irreversibly. Once a coherent mass is formed, it becomes very difficult to dispose of the blood and to clean the area of the spillage. In addition, the effervescent powdered product can only be used on spillages on horizontal or nearly horizontal surfaces.

Also, it is not easy to dose a powdered product correctly, to the extent that an effective disinfection is achieved. Finally, a powdered product may contain dusty components which may render it hazardous to handle, as it is essentially a rather aggressive chemical composition.

It is therefore one objective of the present invention to provide an article for treating and disinfecting spillages of blood and other body fluids, which article does not possess the above-mentioned disadvantages.

Another objective of the present invention is to provide a method of disinfecting liquid spillages which does not exhibit the drawbacks of the known methods.

It has now been found that these objectives can be achieved by the present invention. According to one aspect of the present invention, there is provided a package containing a sheet-like article for wiping surfaces, said article comprising a highly absorbent material capable of absorbing and retaining a hydrophilic liquid and of reversibly releasing at least some of that liquid on the application of hand pressure, and further containing an anti-viral agent, whereby the highly absorbent material is contained between two sheets of material, at least one of them being permeable to the liquid.

The sheet-like article is contained in a package, which is preferably a re-sealable, watertight plastic bag, such as a bag made of heavy-duty polyethylene having skirt-welded seams and a re-sealable closure of the tongue-and-groove type. The wipe comprises a highly absorbent material, which in principle may be any highly absorbent material, such as cellulose foam, or a polyvinyl formal foam, such as the material commercially available from Kanebo Ltd. However, it is essential for the proper functioning of the sheet-like article that it is capable of absorbing and retaining a hydrophilic liquid, without dripping, until said liquid is needed to disinfect a surface contaminated with blood, urine or other body fluids which may be infectious. At that moment, the liquid is reversibly released from the wipe in a controlled fashion by moderate squeezing. Thereafter, the wipe is used to reabsorb the liquid which is now mixed with the spillage.

According to a preferred embodiment of the invention, the highly absorbent material is the polymerization product of a high internal phase emulsion having an aqueous internal phase and a continuous phase comprising one or more polymerisable hydrophobic monomers (a so-called Polyhipe ® material). Such materials and wipes carrying such materials are described in more detail in the European patent applications 60,138 and 68,830, which are incorporated herein by reference. Vinyl polymers are of especial interest, styrene homo- and co-polymers being preferred. Especially sulphonated Polyhipe materials proved to be suitable. The Polyhipes can be used both in their collapsed and their noncollapsed form, but the non-collapsed are greatly preferred.

The highly absorbent material is contained between two sheets of material. In principle, a large variety of fabrics, woven or non-woven, are suitable for this purpose. However, it is essential that at least one of these sheets is permeable to water, so that in use the highly absorbent material is readily brought into contact with the spillage. It is thereby advantageous if the permeable sheet is also hydrophilic, as this facilitates the passage of water through the sheet.

In order to obtain a scouring action when mopping up the spillage, one permeable sheet is preferably equipped with abrasive particles. It is advantageous when the two sides have different colours, so that a distinction between them can be easily made. These abrasive particles comprise granules of a synthetic polymeric material such as polystyrene, polymethyl methacrylate, polyvinyl chloride or, preferably, polyamide. The application of these and other abrasive materials to the surface of wipes is described in the European patent application 211,664.

A further essential ingredient of the wipe is the anti-viral agent. This compound must be capable of irreversibly inactivating most known dangerous viruses, such as HIV (which may cause AIDS) and the Hepatitis B virus. The anti-viral agent is defined in the present invention as a chemical compound or composition or a precursor thereof, which in solution is capable of irreversibly inactivating pathogenic viruses, for humans as well as for animals, which viruses may be present in liquid spillages of body fluids.

There is no universal standard test known to us which especially applies to disinfecting surfaces from pathogenic viruses. However, the joint guideline of the German Bundesgesundheitsamt and the Deutsche Vereinigung zur Bekämpfung der Viruskrankheiten, "Richtlinie des Bundesgesundheitsamtes und der Deutschen Vereinigung zur Bekämpfung der Viruskrankheiten zur Prüfung von chemischen Desinfektionsmittln auf Wirksamkeit gegen Viren", Bundesgesundheitsblatt 25, 397–398 (1982), provides a method of assessing the anti-viral activity of a chemical compound in a suspension test. According to this method, a compound is regarded as an anti-viral agent if it is capable of reducing the infectivity of a virus suspension by a factor of at least $10^4$.

It will be readily understood that the man skilled in the art will be capable of selecting suitable compounds for carrying out the invention by carrying out the test described in the aforementioned publication. It can, of course, not be excluded that certain compounds which do not fulfill the requirements of the above test but which are otherwise known as anti-viral agents, may also be effective in the present invention.

An example of a suitable anti-viral agent is the non-ionic compound Nonidet P-40 (octyl phenol ethoxylate - 9EO), which was shown to be effective in killing the AIDS-virus (L. Resnick et al., J. Am. Med. Assoc. 225, 14 (1986), 1887-1891).

The anti-viral agent is preferably a hypohalite, hypochlorite being especially preferred. This compound cannot be incorporated in the wipe, since it is not stable in an aqueous solution and it may also react with the wipe material.

Therefore the hypohalite is generated in the wipe at or shortly before the moment of use. To that end, the wipe contains a dry compound, preferably in the form of non-dusty granules, which generates a hypohalite upon contact with water, for example an alkali metal dichloroisocyanurate, preferably sodium dichloroisocyanurate dihydrate.

When the wipe is brought into contact with the aqueous spillage, the anti-viral agent could be generated and the spillage as well as the area which it covers would be disinfected.

According to a preferred embodiment of the invention, however, there is provided an amount of water, separated from the hypohalite-generating compound by a water-impermeable, removable or rupturable barrier, said barrier being removed or ruptured at the point of use to generate the hypohalite solution. More specifically, the package contains a separate, rupturable or openable container wherein a sufficient amount of water is provided to generate an effective concentration of at least 0.5% (w/w), preferably at least 2% (w/w) of active chlorine. The absorbent capacity of the wipe is thereby chosen such that the dilution upon contacting the spillage is not greater than a factor of 2, corresponding to a concentration of at least 0.25% by weight active chlorine. The water in the container may also contain a small amount of a detergent and/or abrasive, which must be compatible with the anti-viral agent.

Preferably, the container is a plastic bottle having a twist-off top. Before usage, the bottle containing the water must be opened while it is still contained in the closed package. This can be easily achieved by twisting the top off. Then the amount of water is absorbed by the wipe by squeezing it several times until it is thoroughly soaked. The package is opened after approximately 5-30 sec. and the wipe, which now contains an effective amount of active chlorine, is applied to the spillage.

In principle, it is also possible to incorporate the water in the sheet-like article and to provide the anti-viral agent in the rupturable or openable container. In use, such sheet-like article will equally become charged with the anti-viral agent.

According to another aspect of the present invention there is provided a method of disinfecting a liquid spillage, in particular blood. This method is characterized in that a package according to the invention is used by first breaking the breakable water-containing bag and waiting for 5-30 seconds, if such bag is provided, subsequently opening the package and taking out the sheet-like article, squeezing it slightly to liberate some of the anti-viral agent and wiping the spillage, whereafter the hand pressure is released to absorb as much of the spillage as possible into the sheet-like article.

The invention will now be further illustrated by means of the following examples, which are not meant as limiting the invention in any respect.

EXAMPLE 1

A wipe of 12×12 cm was manufactured using on one side a hydrophilic spun-bonded viscose non-woven fabric sold by Mitsubishi under the trade mark TCF 406. The fabric was equipped with polyethylene beads on one side according to standard techniques by uniformly covering it with 0.6 g polyethylene beads. Subsequently, the sheet was placed in an oven at 140° C. for 2 minutes, removed and allowed to cool. The fabric weighed 100 grams per $m^2$. The other side of the wipe consisted of a smooth hydrophobic sheath of polypropylyene, sold by Kimberley-Clark under the trade mark Kimtex EHP. This fabric weighed 60 grams per $m^2$. The TCF 406 fabric and the Kimtex EHP were placed together, the polyethylene-covered side facing the Kimtex EHP. The two fabrics were welded together by applying heat under pressure along 3 edges of the fabrics to form an open pouch.

3.5 g sodium dichloroisocyanurate dihydrate and 3.0 g of a Polyhipe material, consisting of a non-collapsed sulphonated polystyrene/divinyl benzene material, 90% void volume and containing approximately 0.7 $SO_3$ moiety per benzene ring were put into the pouch, which was subsequently heat-sealed along the fourth side to form a closed pouch.

The wipe was placed in a re-sealable polyethylene bag together with a rupturable sachet containing 46.5 g water.

EXAMPLE 2

A wipe of 12×12 cm was manufactured using on one side a hydrophilic viscose non-woven fabric sold by Bonded Fibre Fabric, U.K., under the trade mark EVA 40 KP. The fabric was equipped with polyamide beads on one side and weighed 40 grams per $m^2$. The other side of the wipe consisted of a smooth hydrophilic viscose non-woven fabric, sold by Bonded Fibre Fabric under the trade mark PRR 55. This fabric weighed 55 grams per $m^2$. It was printed with a blue diamond pattern for ready distinction. On one side it was covered by a layer of sinter-coated polyethylene particles. The EVA 40 KP fabric and the PRR 55 were placed together, the polyethylene-covered side facing the EVA, with the polyamide beads facing outwards. The two fabrics were welded together by applying heat under pressure along 3 edges of the fabrics to form an open pouch.

3.6 g sodium dichloroisocyanurate dihydrate and 2.6 g of a granular Polyhipe material, consisting of a non-collapsed sulphonated polystyrene/divinyl benzene, 90% void volume and containing approximately 0.7 $SO_3$ moiety per benzene ring, were put into the pouch. The pouch was subsequently heat-sealed along the fourth side to form the wipe.

The wipe was placed in a re-sealable, skirt-welded polyethylene bag together with a plastic bottle having a twist-off neck and containing 50.0 g sterile water. The bag was then sealed.

EXAMPLE 3

A package containing the wipe described in Example 2 was used to clean and disinfect a melamine-topped bench on which samples of fresh human blood were applied. The blood was obtained from a male volunteer.

1 ml blood was spread on the bench, using an Eppendorff pipette having a disposable tip.

First, a pair of disposable plastic gloves was put on. Then the water bottle was opened by twisting off the top, while it was still in the sealed bag. The wipe was activated by squeezing it 5–10 times, whereby the wipe was thoroughly wetted and the dichloroisocyanurate dissolved completely.

Approximately 20 seconds after the water bottle was opened, the wetted wipe which now contained hypochlorite was taken out of the package. The wipe was slightly squeezed to liberate some of the anti-viral solution which was applied to the blood on the surface. The blood was wiped first with the abrasive side to loosen any dried blood, and subsequently any residues were mopped up with the smooth side.

Another 1 ml of blood was spread on the bench and it was mopped up using the same wipe. The procedure was repeated until the blood could no longer be mopped up completely. It was found that a single wipe of $12 \times 12$ cm containing 3 g of polyhipe could be used to mop up at least 6 ml blood before its capacity was exhausted.

After the mopping up, the wipe was put into the resealable polyethylene bag again together with the disposable gloves. Subsequently the package was sealed and disposed of.

The area on the bench on which the blood had been spread was effectively cleaned and showed no traces of blood.

EXAMPLE 4

The anti-viral activity of the wipes according to the present invention was tested as follows. A wipe according to Example 1 was used. The anti-viral solution was recovered from the wipe by squeezing the liquid into a container after activation. As a control, a wipe containing only Polyhipe was also tested in the same way, to ensure that the anti-viral effect was not due to residues of the Polyhipe. As a further control, a solution of 4.2% formaldehyde was used.

The anti-viral activity of the solutions thus obtained was assessed in a suspension test which was carried out according to the guidelines of the Deutsche Vereinigung zur Bekämpfung der Viruskrankheiten (also published in: Hygiene and Medicine 9, 177 (1982)). Poliovirus was used as the indicator virus. Poliovirus type 1 (Mahoney strain) was obtained from Natec, Hamburg, and the Vero cell line (Green Monkey Kidney) was purchased from Flow Laboratories.

The poliovirus was grown in confluent layers of Vero until complete cytopathic effect was observed. Cultures were then frozen and thawed, after which they were centrifuged to remove cell debris. The supernatant was stored in aliquots at $-70°$ C. The virus content of the suspension was determined by titration.

Monolayers of Vero cells were cultured in 96 well microtitre plates in a 5% carbon dioxide atmosphere. Ten-fold dilutions of virus suspension were made in maintenance medium. One hundred microlitres of each dilution was added to a single well, five replicates of each dilution were made. Cell controls were included on every plate. The plates were incubated at 37° C. in a $CO_2$ incubator and observed daily and discarded after seven days. The virus titre was calculated from the Kärber formula (Lenette, E.H. and Schmidt, N.J., Diagnostic Procedures for Viral, Rikettsial and Chlamydial Infections, 5th Edition, p. 32–35 (1979)).

The suspension tests were carried out at room temperature (20° C.), but, after appropriate contact times, dilutions were made in ice cold medium. A virus suspension of known titre of at least $10^8$ $TCID_{50}$ (50 per cent tissue culture infectious dose) was used.

One part of virus suspension was mixed with one part distilled water and eight parts of anti-viral solution. The mixture was kept at 20° C. for the duration of the contact time. The following contact times were used: 2, 5, 15, 30 and 60 minutes.

After appropriate contact times, samples were taken and an initial 1:100 dilution was made by adding 0.1 ml to 9.9 ml medium, subsequent dilutions being made by adding 0.1 ml to 0.9 ml. All dilutions were made in ice cold medium, and the tubes containing dilutions were kept on ice until inoculated into cell cultures. One hundred microlitres per well, five replicates for each dilution.

The microtitre plates were incubated at 37° C. in an incubator with a 5% $CO_2$ atmosphere, and examined daily until they were discarded on day 7. The virus titre for each contact time was calculated as before from the Kärber formula.

The results from the suspension tests are shown in FIG. 1.

It is clear from FIG. 1 that the anti-viral solution from the wipe achieved a reduction of more than $10^4$ in the virus titre, at all contact times. The 4.2% formaldehyde solution achieved a similar effect, provided the contact time was five or more minutes. The control wipe solution, containing only water squeezed from the wipe, behaved like pure water and did not show any anti-viral activity.

We claim:

1. Package containing a sheet-like article for wiping surfaces, said article comprising an absorbent material capable of absorbing and retaining a hydrophilic liquid, and of reversibly releasing at least some of the liquid on application of hand pressure, said absorbent material being the polymerization product of an internal phase emulsion having an aqueous internal phase and a continuous phase comprising one or more polymerizable hydrophobic monomers, said article further containing an anti-viral agent, whereby the absorbent material is contained between two sheets of material, at least one of them being permeable to the liquid.

2. Package according to claim 1, wherein the absorbent material is a sulphonated polymerization product.

3. Package according to claim 1, wherein the sulphonated polymerization product is in a non-collapsed form.

4. Package according to claim 1, wherein the antiviral agent is a compound which generates a hypohalite on contact with water.

5. Package according to claim 1, wherein the hypohalite is hypochlorite.

6. Package according to claim 1, wherein the antiviral agent is an alkali metal dichloro-isocyanurate.

7. Package according to claim 1, wherein the absorbent material is contained between two sheets of material, at least one of them being permeable to the liquid and hydrophilic.

8. Package according to claim 1, wherein at least one of the surfaces of the sheet-like articles is coated with abrasive particles.

9. Package according to claim 1, wherein the antiviral agent is sodium dichloroisocyanurate dihydrate.

* * * * *